United States Patent
Zhao et al.

(10) Patent No.: US 12,209,244 B2
(45) Date of Patent: Jan. 28, 2025

(54) INNOVATIVE METHOD FOR IMPROVING ENZYME ACTIVITY OF NMN BIOSYNTHETIC ENZYME NAMPT

(71) Applicant: HOBOOMLIFE BIO-TECHNOLOGY (SHENZHEN) CO., LTD., Shenzhen (CN)

(72) Inventors: Liqing Zhao, Shenzhen (CN); Jiansheng Chen, Shenzhen (CN); Zhigang Duan, Shenzhen (CN); Haichao Zhang, Shenzhen (CN); Beijia Huang, Shenzhen (CN)

(73) Assignee: HOBOOMLIFE BIO-TECHNOLOGY (SHENZHEN) CO., LTD., Guangdong (CN)

( * ) Notice: Subject to any disclaimer, the term of this patent is extended or adjusted under 35 U.S.C. 154(b) by 0 days.

(21) Appl. No.: 17/934,025

(22) Filed: Sep. 21, 2022

(65) Prior Publication Data

US 2023/0022968 A1    Jan. 26, 2023

Related U.S. Application Data

(62) Division of application No. 17/489,767, filed on Sep. 29, 2021, now Pat. No. 11,492,627.

(30) Foreign Application Priority Data

Apr. 28, 2021   (CN) .......................... 202110468908.5

(51) Int. Cl.
| | | |
|---|---|---|
| *C12N 15/50* | (2006.01) | |
| *C12N 9/10* | (2006.01) | |
| *C12N 15/52* | (2006.01) | |
| *C12N 15/70* | (2006.01) | |

(52) U.S. Cl.
CPC ........... *C12N 15/52* (2013.01); *C12N 9/1077* (2013.01); *C12N 15/70* (2013.01); *C12Y 204/02012* (2013.01)

(58) Field of Classification Search
CPC . C12N 1/20; C12N 9/24; C12P 19/305; C12P 19/30; C12P 13/00; C12Y 207/06001; C12Y 401/9901
See application file for complete search history.

(56) References Cited

U.S. PATENT DOCUMENTS

2018/0230443 A1    8/2018  Fu et al.

FOREIGN PATENT DOCUMENTS

| CN | 108026517 A | 5/2018 |
| CN | 110373397 A | 10/2019 |
| CN | 111718915 A | 9/2020 |

OTHER PUBLICATIONS

Witkowski, Andrzej, et al; Conversion of a Beta-Ketoacyl Synthase to a Malonyl Decarboxylase by Replacement of the Active Site Cysteine with Glutamine; Bochemistry 1999; vol. 38; pp. 11643-11650.
Kisselev, Lev; Polypeptide Release Factors in Prokaryotes and Eukaryotes: Same Function, Different Structure; Structure, vol. 10, Jan. 2002, pp. 8-9.
Devos, Damien et al.; Practical Limits of Function Prediction; Proteins: Structure, Function, and Genetics 41: pp. 98-107 (2000).
Whisstock, James C., et al; Prediction of protein function from protein sequence and structure; Quarterly Reviews of Biophysics; vol. 36, No. 3; 2003, pp. 307-340.
Non-Final Office Action issued in U.S. Appl. No. 17/489,767; mailed May 24, 2022; 5 pgs.
Non-Final Office Action issued in U.S. Appl. No. 17/489,767; mailed Feb. 10, 2022; 10 pgs.
Restriction Requirement issued in U.S. Appl. No. 17/489,767; mailed Jan. 11, 2022; 6 pgs.
Notice of Allowance issued in U.S. Appl. No. 17/489,767; mailed Aug. 22, 2022; 8pgs.
TrackOne Request Granted issued in U.S. Appl. No. 17/489,767; dated Oct. 13, 2021; 2 pgs.
Zhang, Sailong; Study of Active Compounds Targeting Nampt; China Academic Journal Electronic Publishing House, May 2016; 109 pgs. (English Abstract).
Wang, Feng et al.; Enzymatic activities of recombinant human Nampt and Nampt (H247A) proteins; Journal of Zhejiang University (Medical Sciences); vol. 40, No. 2, 2011; 156-162 pgs. (English Abstract).
First Office Action and Search Report issued in corresponding Chinese Application No. 202110468908.5; mailed Aug. 23, 2021; 10 pgs.
Notice of Grant issued in corresponding Chinese Application No. 202110468908.5; mailed Sep. 22, 2021; 3 pgs.

*Primary Examiner* — Tekchand Saidha
*Assistant Examiner* — Mohammad Y Meah
(74) *Attorney, Agent, or Firm* — HAUPTMAN HAM, LLP (57) ABSTRACT

The present disclosure provides an innovative method for improving the enzyme activity of an NMN biosynthetic enzyme Nampt, and relates to the technical field of genetic engineering. A mutant protein of the present disclosure is obtained by firstly analyzing a target protein Nampt using two softwares FoldX and DeepDDG, and then predicting multiple key sites influencing the enzyme functions and finally performing the semi-rational design of the enzyme. In the examples of the present disclosure, 10 mutant strains are constructed using the designed primers according to the principle of point mutation, and 8 of the mutants have higher activity than a wild-type strain, in which the NMN yield of the mutant Nampt-V365L is increased by 62%, and the NMN yields of the mutants Nampt-S248A, Nampt-N164L, Nampt-S382M, Nampt-A245T and Nampt-A208G are increased by 34%, 27%, 27%, 22% and 17% respectively.

6 Claims, 2 Drawing Sheets

Specification includes a Sequence Listing.

INNOVATIVE METHOD FOR IMPROVING ENZYME ACTIVITY OF NMN BIOSYNTHETIC ENZYME NAMPT

CROSS REFERENCE TO RELATED APPLICATION(S)

The present application is a Divisional Application of U.S. application Ser. No. 17/489,767, filed on Sep. 29, 2021, which claims priority to Chinese Patent Application No. 202110468908.5, filed on Apr. 28, 2021. The disclosures of the aforementioned applications are hereby incorporated by reference in their entireties.

INCORPORATION BY REFERENCE

The sequence listing provided in the file entitled PO1220746P_USQ_1_Sequence_Llisting_pdated.xml, which is an Extensible Markup Language (XML) file that was created on Sep. 21, 2022, and which comprises 45,792 bytes, is hereby incorporated by reference in its entirety.

TECHNICAL FIELD

The present disclosure belongs to the technical field of genetic engineering, and in particular relates to an innovative method for improving the enzyme activity of an NMN biosynthetic enzyme Nampt.

BACKGROUND

Nicotinamide mononucleotide (NMN) is an organic molecule as well as a nucleotide, which has the functions of reversing aging and extending life.

At present, the synthesis of nicotinamide mononucleotide is realized mostly through an enzymatic reaction. Natural niacinamide phosphoribosyltransferase (Nampt) has a shortcoming of relatively low enzyme activity, which results in a high cost of a traditional enzymatic reaction, harsh reaction conditions, an unstable production process, a great difference in index among each batch of products, and low productivity of the reaction; and consequently, large-scale industrial production is hard to realize and large-scale application of NMN is restricted.

SUMMARY

To this end, an objective of the present disclosure is to provide an innovative method for improving the enzyme activity of an NMN biosynthetic enzyme Nampt, and specifically to provide a recombinant expression vector encoding a mutant protein of Nampt, recombinant bacteria and a Nampt mutant protein, in which after the Nampt mutant protein is expressed by the recombinant bacteria, the enzyme activity is significantly improved, and large-scale industrial production can be realized.

To achieve the above-mentioned objective, the present disclosure provides the following technical solution:

The present disclosure provides a mutant protein of a nicotinamide phosphoribosyltransferase Nampt, which is configured to perform a point mutation on an amino acid sequence of the nicotinamide phosphoribosyltransferase Nampt. The amino acid sequence of the nicotinamide phosphoribosyltransferase Nampt includes a sequence shown in SEQ ID NO:1; and sites of the point mutation include: N67K, N164L, R166W, A208G, A245T, S248A, V365L or S382M.

The present disclosure further provides a recombinant expression vector including a nucleotide sequence encoding the above-mentioned mutant protein.

Preferably, a basic vector of the recombinant expression vector includes a pPSUMO vector.

The present disclosure further provides recombinant bacteria expressing the mutant protein or including the above-mentioned recombinant expression vector.

Preferably, a basic strain of the recombinant bacteria includes *Escherichia coli*.

The present disclosure further provides a construction method for the recombinant bacteria, including the following steps: (1) performing codon optimization on a gene encoding the amino acid sequence shown in SEQ ID NO:1, to obtain an optimized gene;
(2) performing a PCR amplification using a site-directed mutation primer and a high-fidelity enzyme respectively by taking the optimized gene as a template, to obtain amplification products;
(3) digesting the amplification products with a DpnI enzyme respectively, and then connecting to the pPSUMO vector respectively, to obtain a recombinant expression vector; and
(4) transforming the recombinant expression vector into *E. coli* competent cells respectively, and picking positive clones, to obtain the recombinant bacteria.

Preferably, a nucleotide sequence of the optimized gene in step (1) includes a sequence shown in SEQ ID NO:2.

Preferably, the site-directed mutation primers in step (2) include: site-directed mutation primers N67K-F and N67K-R directed at a point mutation of N67K, a nucleotide sequence of the N67K-F shown in SEQ ID NO:3, and a nucleotide sequence of the N67K-R shown in SEQ ID NO:4;

site-directed mutation primers N164L-F and N164L-R directed at a point mutation of N164L, a nucleotide sequence of the N164L-F shown in SEQ ID NO:5, and a nucleotide sequence of the N164L-R shown in SEQ ID NO:6;

site-directed mutation primers R166W-F and R166W-R directed at a point mutation of R166W, a nucleotide sequence of the R166W-F shown in SEQ ID NO:7, and a nucleotide sequence of the R166W-R shown in SEQ ID NO:8;

site-directed mutation primers A208G-F and A208G-R directed at a point mutation of A208G, a nucleotide sequence of the A208G-F shown in SEQ ID NO:9, and a nucleotide sequence of the A208G-R shown in SEQ ID NO:10;

site-directed mutation primers A245T-F and A245T-R directed at a point mutation of A245T, a nucleotide sequence of the A245T-F shown in SEQ ID NO:11, and a nucleotide sequence of the A245T-R shown in SEQ ID NO:12;

site-directed mutation primers S248A-F and S248A-R directed at a point mutation of S248A, a nucleotide sequence of the S248A-F shown in SEQ ID NO:13, and a nucleotide sequence of the S248A-R shown in SEQ ID NO:14;

site-directed mutation primers V365L-F and V365L-R directed at a point mutation of V365L, a nucleotide sequence of the V365L-F shown in SEQ ID NO:15, and a nucleotide sequence of the V365L-R shown in SEQ ID NO:16; and site-directed mutation primers S382M-F and S382M-R directed at a point mutation of S382M, a nucleotide sequence of the S382M-F shown in SEQ ID NO:17, and a nucleotide sequence of the S382M-R shown in SEQ ID NO:18.

Preferably, a procedure of the PCR amplification in step (2) includes: initial denaturation at 94° C. for 2 min, denaturation at 98° C. for 10s, annealing at 55-65° C. for 30s, and extension at 68° C. for 4 min, 30 cycles; and extension at 68° C. for 4 min.

Preferably, picking positive clones in step (4) includes: performing a bacterial liquid PCR using Nampt-F and Nampt-R, a nucleotide sequence of the Nampt-F shown in SEQ ID NO: 23, and a nucleotide sequence of the Nampt-R shown in SEQ ID NO: 24.

The present disclosure provides a mutant protein of a nicotinamide phosphoribosyltransferase. The mutant protein is obtained by firstly analyzing a target protein Nampt using two softwares FoldX and DeepDDG, and then predicting multiple key sites influencing the enzyme functions, and finally performing the semi-rational design of the enzyme. In the examples of the present disclosure, 10 mutant strains constructed with the designed primers according to the principle of point mutation indicates by sequencing and verifying that they all mutate successfully on a given site, thereby indicating successful cloning of the 10 mutant strains. Among the 10 cloned mutants, 8 mutants have higher activity than a wild-type (E. coli DH5 α-ppsumo-Nampt) strain, and the mutant Nampt-V365L has the highest activity, with an NMN yield at 45.42 mg/L, an increase of 62% from that (28.11 mg/L) of the wild-type strain. The NMN yields of mutants Nampt-S248A, Nampt-N164L, Nampt-S382M, Nampt-A245T and Nampt-A208G are increased by 34%, 27%, 27%, 22% and 17% compared to the wild-type strain, while the NMN yields of Nampt-V467L and S155I are reduced by 53% and 31% respectively.

DETAILED DESCRIPTION

The present disclosure provides a mutant protein of a nicotinamide phosphoribosyltransferase Nampt configured to perform point mutation on the amino acid sequence of the nicotinamide phosphoribosyltransferase Nampt, in which the amino acid sequence of the nicotinamide phosphoribosyltransferase Nampt includes a sequence shown in SEQ ID NO:1: GNAAAEAEFNIL-LATDSYKVTHYKQYPPNTSKVYSYFECREKKT ENSKVRKVKYEETVFYGLQYILN-KYLKGKVVTKEKIQEAKEVYREHFQDDVFNERGWN YILE-KYDGHLPIEVKAVPEGSVIPRGNVLFTVENTDPE-CYWLTNWIETILVQSWYPITVAT NSREQKKILAKYL-LETSGNLDGLEYKLHDFGYRGVSSQETAGIGASAHL-VNFKGTDTVA GIALIKKYYGTKDPVPGYSVPAAEH-STITAWGKDHEKDAFEHIVTQFSSVPVSVVSDSYD IYNACEKIWGEDLRHLIVSRSTEAPLIIRPDSGN-PLDTVLKVLDILGKKFPVTENSKGYKLL PPYLRVIQGDGVDINTLQEIVEG-MKQKKWSIENVSFGSGGALLQKL-TRDLLNCSFKCSYV VTNGLGVNVFKDPVADPNKR-SKKGRLSLHRTPAGNFVTLEEGKGDLEEYGHDL-LHTVF KNGKVTKSYSFDEVRKNAQLNIEQDVAPH; and sites of the point mutation include: N67K, N164L, R166W, A208G, A245T, S248A, V365L or S382M.

The present disclosure preferably integrates the methods of sequence-based conservation analysis and structure-based Gibbs free energy change analysis and employs two softwares FoldX and DeepDDG to predict a high-quality mutation site. The software FoldX simulates the influence of the mutation site on the protein unfolding free energy ($\Delta G$) using a bioinformatics method. If the mutant $\Delta G$ (mutant) is less than the wild-type $\Delta G$ (wild), the mutation has a positive role on the thermal stability of the protein. If $\Delta G$ is increased after mutation, the mutation site is unfavorable for the stability of the protein. The software DeepDDG in protein engineering can accurately predict a change in the protein stability caused by point mutation. DeepDDG analysis is a method based on a neutral network, and the neutral network has already been tested on more than 5,700 manually planned experimental data points. As for three independent test sets, the Pearson's correlation coefficient is 0.48-0.56. The results of the software analysis indicate that the solubility of a mutant residue and the contact area are the most important features, which indicates that the buried hydrophobic area is a major factor determining the protein stability. With the above-mentioned method, a total of 10 mutation sites are selected in the examples of the present application, namely, N67K, S155I, N164L, R166W, A208G, A245T, S248A, V365L, S382M and V467L, and changes of the above-mentioned 10 mutation sites in the amino acid and nucleotide sequence are shown in Table 1.

TABLE 1

Changes in amino acid and nucleotide sequence in point mutation

| Site | Changes of amino acid | Base changes | Site | Changes of amino acid | Base changes |
| --- | --- | --- | --- | --- | --- |
| N67K | N→K | aac-aaa | A245T | A→T | gct-acc |
| N164L | N→L | aac-ctg | S248A | S→A | tca-gcg |
| R166W | R→W | cgc-tgg | V365L | V→L | gtt-ctg |
| A208G | A→G | gct-ggc | S382M | S→M | tca-atg |
| S155I | S→I | tca-atc | V467L | V→L | gta-ctg |

The present disclosure further provides a recombinant expression vector including a nucleotide sequence encoding the above-mentioned mutant protein.

A basic vector of the recombinant expression vector of the present disclosure preferably includes a pPSUMO vector, and the nucleotide sequence encoding the mutant protein is preferably connected between the HindIII and NdeI enzyme digestion sites of the pPSUMO vector.

The present disclosure further provides recombinant bacteria expressing the mutant protein or including the above-mentioned recombinant expression vector.

A basic strain of the recombinant bacteria of the present disclosure preferably includes *Escherichia coli*.

The present disclosure further provides a construction method for the recombinant bacteria, including the following steps: (1) performing codon optimization on a gene encoding the amino acid sequence shown in SEQ ID NO:1, to obtain an optimized gene;

(2) performing a PCR amplification using a site-directed mutation primer and a high-fidelity enzyme respectively by taking the optimized gene as a template, to obtain amplification products;

(3) digesting the amplification products with a DpnI enzyme respectively, and then connecting to the pPSUMO vector respectively, to obtain a recombinant expression vector; and (4) transforming the recombinant expression vector into *E. coli* competent cells respectively, and picking positive clones, to obtain the recombinant bacteria.

The present disclosure performs codon optimization on a gene encoding the amino acid sequence shown in SEQ ID NO:1, to obtain an optimized gene. The present disclosure preferably adopts a codon fitting the *E. coli* preference to carry out codon optimization, and the nucleotide sequence of the obtainedoptimized gene includes a sequence (1,482 bp) shown in SEQ ID NO:2: CATATGAACGCTGCTGAGGCCGAGTTCAATATATTGT TAGCGACCGACTCGTACAAGGTCACGCATTATAAACAGTATCCTCCTAACACATCAA AGGTCTACTCATATTTCGAGTGCCGCGAGAAGAAGACGGAGAACTCGAAAGTCCGA AAGGTGAAGTATGAAGAAACAGTGTTCTACGGGCTTCAGTATATTCTTAACAAATAT CTTAAAGGCAAAGTTGTTACAAAGGAGAAGATCCAGGAAGCTAAAGAAGTTTATCG CGAACATTTCCAAGACGATGTCTTCAATGAGCGCGGCTGGAACTATATTCTTGAGAA GTACGACGGCCATCTTCCTATTGAAGTTAAAGCTGTTCCTGAAGGCTCAGTTATTCCT CGCGGCAACGTCCTGTTTACCGTCGAGAATACGGATCCTGAATGTTATTGGCTTACA AACTGGATTGAAACAATTCTTGTTCAGTCATGGTATCCTATTACAGTTGCTACAAACT CACGCGAACAGAAGAAGATCCTAGCTAAATATCTTCTTGAAACATCAGGCAACCTTG ATGGCCTTGAATATAAACTTCATGATTTCGGGTACCGCGGCGTTTCATCACAGG AAA CAGCTGGCATTGGCGCTTCAGCTCATCTTGTTAACTTTAAAGGCACAGATACAGTTG CTGGCATTGCTCTTATTAAGAAGTACTACGGCACAAAGGACCCAGTTCCTGGTTATT CAGTTCCTGCTGCTGAACATTCAACAATTACAGCTTGGGGAAAGGATCATGAGAAGG ACGCGTTCGAGCACATTGTTACACAGTTCAGTAGTGTTCCTGTTTCAGTTGTTTCAGA TTCTTATGATATTTATAACGCTTGTGAGAAGATCTGGGGAGAGGACCTTCGCCATCTT ATTGTTTCACGCTCAACAGAAGCTCCTCTTATTATTCGCCCTGATTCAGGCAACCCTC TTGATACAGTTCTTAAAGTTCTTGATATTCTTGGCAAGAAGTTCCCGGTTACCGAGAA TTCCAAGGGTTATAAACTTCTTCCTCCTTATCTTCGCGTTATTCAGGGCGATGGCGTT GATATTAACACACTTCAGGAAATTGTTGAAGGCATGAAACAGAAGAAGTGGTCCATT GAGAATGTCTCATTTGGCTCAGGCGGCGCTCTTCTTCAGAAACTTACACGCGATCTTC TTAACTGTTCATTTAAATGTTCTTATGTTGTTACAAACGGCCTTGGCGTTAACGTGTT CAAAGATCCCGTAGCAGACCCTAACAAACGCTCAAAGAAGGGTCGACTTTCACTTCA TCGCACACCTGCTGGCAACTTTGTTACACTTGAAGAAGGCAAAGGCGATCTTAAGA ATATGGCCATGATCTTCTTCATACAGTGTTCAAGAATGGCAAGGTAACGAAGTCCTA CTCATTTGATGAAGTTCGCAAGAATGCGCAGCTTAACATTGAACAGGATGTTGCTCC TCATAAGCTT.

After the optimized gene is obtained, the present disclosure performs PCR amplification using a site-directed mutation primer and a high-fidelity enzyme by taking the optimized gene as a template, to obtain amplification products. The high-fidelity enzyme of the present disclosure preferably includes a KOD-Plus-Neo enzyme, which is purchased from Toyobo (Shanghai) Biotech Co., Ltd.

The preferred information of the site-directed mutation primer of the present disclosure is shown in Table 2:

TABLE 2

Information of site-directed mutation primer

| Primer name | Primer sequence (5' to 3') | SEQ ID NO: | Tm (° C.) |
|---|---|---|---|
| N67K-F | cgggcttcagtatattcttaaaaaatatcttaaagg | 3 | 56 |
| N67K-R | tttaagaatatactgaagcccgtagaacactGT | 4 | 60 |
| S155I-F | ggattgaaacaattcttgttcagatctggtatccta | 19 | 53 |
| S155I-R | gatctgaacaagaattgtttcaatccagtttg | 20 | 59 |
| N164L-F | cctattacagttgctacactgtcacgcgaac | 5 | 54 |
| N164L-R | cagtgtagcaactgtaataggataccat | 6 | 53 |
| R166W-F | gttgctacaaactcatgggaacagaagaag | 7 | 56 |
| R166W-R | ccatgagtttgtagcaactgtaataggatacc | 8 | 57 |
| A208G-F | ggaaacagctggcattggcggctcagctcatct | 9 | 63 |
| A208G-R | gccgccaatgccagctgtttcctgtgatgaaac | 10 | 66 |
| A245T-F | cctggttattcagttcctgctaccgaacattcaac | 11 | 57 |
| A245T-R | ggtagcaggaactgaataaccaggaactg | 12 | 61 |
| S248A-F | tcctgctgctgaacatgcgacaattacag | 13 | 56 |

TABLE 2-continued

Information of site-directed mutation primer

| Primer name | Primer sequence (5' to 3') | SEQ ID NO: | Tm (° C.) |
|---|---|---|---|
| S248A-R | actatgttcagcagcaggaactgaataac | 14 | 60 |
| V365 L-F | attaacacacttcaggaaattctggaaggcatgaaac | 15 | 55 |
| V365L-R | cagaatttcctgaagtgtgttaatatcaacg | 16 | 57 |
| S382M-F | attgagaatgtctcatttggcatgggcggcgctc | 17 | 61 |
| S382M-R | catgccaaatgagacattctcaatggacc | 18 | 60 |
| V467L-F | agtgttcaagaatggcaagctgacgaagtcctactc | 21 | 58 |
| V467L-R | cagcttgccattcttgaacactgtatgaagaag | 22 | 60 |

In the primer design of the present disclosure, mutation sites are preferably located on two primers, namely, on the downstream part of an overlap area of a forward mutation primer and adjacent to the overlap area, and at the 5' end of a backward mutation primer. The primer includes a 5' end overlap area and a 3' end extension area. Except the mutation sites, the length of each primer is about 25-30 bp, the 5' end overlap area includes 15-20 bases, and the 3' end extension area includes at least 10 bases.

The PCR amplification system of the present disclosure, calculated in 50 µL, preferably includes 1.5 µL of mutation primers F/R (10 µM) respectively, 5 µL of 10×PCR Buffer for KOD-Plus-Neo, 5 µL of 2 mM dNTPs, 3 µL of 25 mM MgSO$_4$, DNA template<1 ng, 1 µL of KOD-Plus-Neo (1U/µL), and the balance of ddH$_2$O, adding up to 50 µL. In the present disclosure, the system is prepared preferably on ice, and the KOD-Plus-Neo enzyme is added last, so as to guarantee the enzymee activity. In the present disclosure, a procedure of the PCR amplification preferably includes: initial denaturation at 94° C. for 2 min, denaturation at 98° C. for 10s, annealing at 55-65° C. for 30s, and extension at 68° C. for 4 min, 30 cycles; and extension at 68° C. for 4 min.

After amplification products are obtained, the amplification products are digested with a DpnI enzyme respectively, and then connected to the pPSUMO vector respectively, to obtain a recombinant expression vector. The present disclosure preferably uses a DpnI fast digestion enzyme of the Takara company to eliminate methylation in the template DNA (not mutated), and the enzyme digestion system, calculated in 50 µL, preferably includes: 1 µL of the DpnI enzyme, 5 µL of 10×Quickcut Buffer, the amplification products<1 µL, and the balance of ddH$_2$O, adding up to 50 µL. The digestion of the present disclosure preferably includes: putting the enzyme digestion system in a constant-temperature incubator at 37° C., letting it stand and performing enzyme digestion for 3 h; heating in a metal bath at 85° C. for 5 min; and after the enzyme is deactivated, temporarily storing at 4° C.

In the present disclosure, the amplification products digested by the DpnI enzyme are connected to the pPSUMO vector to obtain the recombinant expression vector, and the connection preferably includes connecting between the HindIII and NdeIenzyme digestion sites of the pPSUMO vector. The present disclosure does not impose special limitations on the connection method, and the connection may be implemented using a conventional method in the art.

After the recombinant expression vector is obtained, the recombinant expression vector is transformed into E. coli competent cells, and positive clones are picked, to obtain the recombinant bacteria.

The present disclosure does not impose special limitations on the transformation method, and the transformation may be implemented using a conventional method in the art. In the screening of positive clones, the present disclosure preferably adopts a sterile toothpick to pick single colony in a panel and puts in 20 µL of sterile ddH$_2$O, then the mixture is heated in a metal bath at 95° C. for 5 min and centrifuged at a high speed of 13,000 rpm for 2 min, and the supernatant can be used as a PCR verification template. After that, the primers Nampt-F (SEQ ID NO:23: taatccttat-tcagtggtggtggtggtggtgctc) and Nampt-R (SEQ ID NO:24: aggaagcttgcatatgaacgctgctgctg) can be utilized to perform bacterial liquid PCR.

In the present disclosure, a system of the bacterial liquid PCR, calculated in 50 µL, preferably includes: 25 µL of Premix Taq, 1 µL of Nampt-F/R respectively, a template<1 ng, and the balance of ddH$_2$O, adding up to 50 µL. In the present disclosure, a procedure of the bacterial liquid PCR preferably includes: initial denaturation at 94° C. for 2 min, denaturation at 98° C. for 10s, annealing at 55° C. for 15s, and extension at 72° C. for 30s, 30 cycles; and extension at 72° C. for 2 min. The present disclosure preferably performs verification sequencing on the positive clones picked by the bacterial liquid PCR, and the positive clones correct according to the sequencing are the recombinant bacteria.

After the recombinant bacteria are obtained, the present disclosure preferably takes the yield of nicotinamide mononucleotide (NMN) as a basis for screening nicotinamide phosphoribosyltransferase (Nampt) positive mutant strains, and a transformation system generating NMN, calculated in 25 µL, preferably includes: 12.5 µL of crude enzyme liquid and 12.5 µL of mother liquid (1 mM NAM, 1 mM PRPP, 1 mM MnCl$_2$ and 1 mM MgCl$_2$). In the present disclosure, the above-mentioned transformation system is mixed evenly, allowed to react for 15 min in a shaking table at a speed of 180 rpm and a temperature of 37° C., and then heated for 1 min in a metal bath at 95° C., to deactivate the enzyme and terminate the reaction. After that, the product is diluted to 500 µL using a PBS buffer solution with pH of 6.0, centrifuged at a speed of 10,000 rpm for 5 min, filtered with a 0.22 µm microporous filter membrane to remove the bacteria, and transferred into a liquid-phase vial; and the yield of NMN is measured by HPLC. It is verified that among the 10 mutants obtained by the present disclosure, the mutants having higher catalytic activity than a wild-type Nampt strain (E.

coli DH5 α-ppsumo-Nampt) are N67K, N164L, R166W, A208G, A245T, S248A, V365L and S382M; and the strains having a decreased catalytic activity are S155I and V476L.

The present disclosure does not impose special limitations on a construction method of the wild-type Nampt strain (*E. coli* DH5 α-ppsumo-Nampt), preferably adopts a method of double enzyme digestion for construction, more preferably adopts a mouse-derived nicotinamide phosphoribosyltransferase (mNampt) sequence (with an amino acid sequence shown in SEQ ID NO:1) synthesized by Suzhou GENEWIZ, and constructs it in a vector pET-30a and clones into the cells *E. coli*-DH5α and *E. coli* BL21 (DE3). The two ends of the target gene contain enzyme digestion sites Hind III and Nde I, and a label 6×His is added to the tail, to obtain *E. coli* DH5 α-ppsumo-Nampt.

The innovative method for improving the enzyme activity of an NMN biosynthetic enzyme Nampt provided by the present disclosure is elaborated below in conjunction with examples, which should not be interpreted as a limit on the protection scope of the present disclosure.

EXAMPLE 1

(1) A strain *E. coli* DH5 α-ppsumo-Nampt preserved in 200 μL of glycerin was sucked with a pipette and inoculated to 20 mL of a LB medium (containing 50 μg/mL kanamycin), and cultured overnight through oscillation in a constant-temperature shaking table at a speed of 200 rpm and a temperature of 37° C.; plasmids were extracted with a kit Plasmid Mini Kit I (100) (purchased from OMEGA).

(2) A PCR amplification system (50 μL) was prepared on ice, and a KOD-Plus-Neo enzyme was added finally to guarantee the enzyme activity: 1.5 μL of mutation primers F/R (10 μM) respectively, 5 μL of 10×PCR Buffer for KOD-Plus-Neo, 5 μL of 2 mM dNTPs, 3 μL of 25 mM $MgSO_4$, a DNA template<1 ng, 1 μL of KOD-Plus-Neo (1U/μL), and the balance of $ddH_2O$, adding up to 50 μL.

The mutation primers involved were the primers shown in Table 2, synthesized by the Aiji Biotechnology Co., Ltd.

A procedure of the PCR amplification was initial denaturation at 94° C. for 2 min, denaturation at 98° C. for 10s, annealing at 55-65° C. for 30s, and extension at 68° C. for 4 min, 30 cycles; extension at 68° C. for 4 min; and storage at 4° C.;

(3) 5 μL of the PCR reaction product was taken and added with 1 μL of 6×Loading Buffer, and transferred by a sample application tip into an agarose gel hole for electrophoresis, and the electrophoresis was performed for 25 min at a voltage of 120 V and at room temperature.

(4) Methylation in the template DNA (not mutated) was eliminated using a DpnI fast digestion enzyme of the Takara company, the enzyme digestion system (50 μL): 1 μL of the DpnI enzyme, 5 μL of 10×Quickcut Buffer, the amplification products in (2)<1 μL, and the balance of $ddH_2O$, adding up to 50 μL. The digestion of the present disclosure preferably included: putting the enzyme digestion system in a constant-temperature incubator at 37° C., letting it stand and performing enzyme digestion for 3 h; heating for 5 min in a metal bath at 85° C.; and after the enzyme is deactivated, temporarily storing at 4° C.; connecting between the enzyme digestion sites Hind III and Nde I of the pPSUMO vector using a method of double enzyme digestion, and then transforming into *E. coli* BL21 (DE3) competent cells.

(5) The recombinant bacteria were introduced into a solid agar medium with resistance against kanamycin (50 μg/mL), single colony in a panel was picked with a sterile toothpick and put in 20 μl of sterile $ddH_2O$, heated for 5 min in a metal bath at 95° C., and centrifuged for 2 min at a high speed of 13,000 rpm, in which the supernatant can be used as a PCR verifying template: 25 μL of Premix Taq, 1 μL of Nampt-F/R respectively, a template<1 ng, and the balance of $ddH_2O$, adding up to 50 μL.

The procedure preferably included: initial denaturation at 94° C. for 2 min, denaturation at 98° C. for 10s, annealing at 55° C. for 15s, and extension at 72° C. for 30s, 30 cycles; extension at 72° C. for 2 min; and storage at 4° C.

Figure 1:
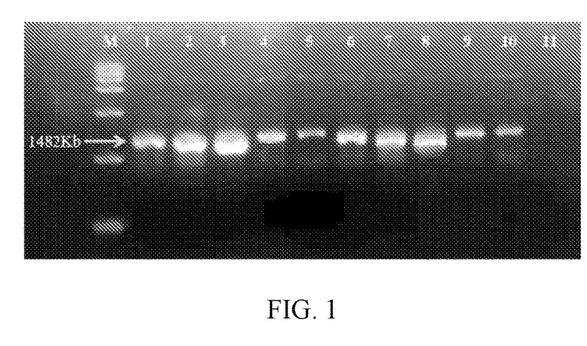
FIG. 1 shows the verification results of colony PCR, in which M: 15,000 DL marker; 1: N67K; 2: S155I; 3: N164L; 4: R166W; 5: A208G; 6: A245T; 7: S248A; 8: V365L; 9: S382M; 10: V467L; 11: negative control.
Figure 2:
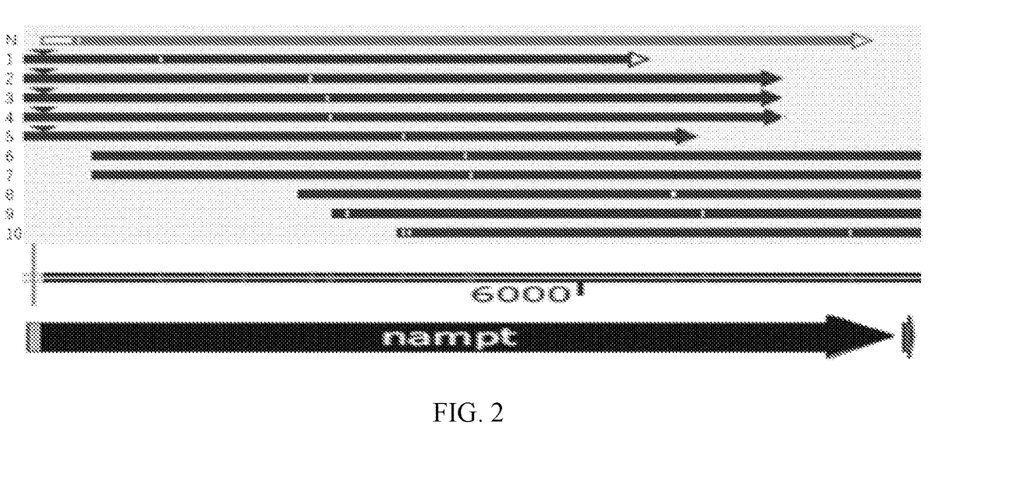
FIG. 2 is a comparison diagram of the sequencing results of mutant strains, in which N is the original sequence of Nampt, and 1-10 are mutant strains, in which 1: N67K; 2: S155I; 3: N164L; 4: R166W; 5: A208G; 6: A245T; 7: S248A; 8: V365L; 9: S382M; 10: V467L; and the white missing parts in the red sequences are the positions of mutation sites.

(6) 1% of the positive clones having stripes verified (at least 3 per panel, FIG. 1) were inoculated in a conical flask (20 mL/50 mL) with a LB kanamycin (50 μg/mL) resistant liquid medium, and cultured for 12 h through oscillation in a constant-temperature shaking table at a speed of 180 rpm and a temperature of 37° C.); next day, 1 mL was taken from each flask and delivered to the Aiji Biotechnology Co., Ltd. for sequencing; the sequencing result (FIG. 2) was compared with that of original Nampt enzyme; and the strains mutated to be consistent with the design were preserved in glycerin. The primers for sequencing are listed in Table 3.

TABLE 3

Sequencing primers at mutation sites

| Sequencing site | Primer name | Primer sequence (5' to 3') | SEQ ID NO. |
|---|---|---|---|
| N67K | CX-67-F | aaaggtctactcatatttcgagtgccg | 25 |
|  | CX-67-R | tctgttcgcgtgagtttgtagca | 26 |
| S155I, N164L | CX-155, 164, 166, 208-F | gtacgacggccatcttcctattga | 27 |
| R166W, A208G | CX-155, 164, 166, 208-R | gaactgggtcctttgtgccgtag | 28 |
| A245T, S248A | CX-245, 248-F | ggcgcttcagctcatcttgttaa | 29 |
|  | CX-245, 248-R | tgaataacgcgaagataaggaggaag | 30 |

TABLE 3-continued

Sequencing primers at mutation sites

| Sequencing site | Primer name | Primer sequence (5' to 3') | SEQ ID NO. |
|---|---|---|---|
| V365L, S382M | CX-365, 382-F<br>CX-365, 382-R | agaggaccttcgccatcttattg<br>aggacttcgttaccttgccattc | 31<br>32 |
| V467L | CX-467-F<br>CX-467-R | gttcaaagatcccgtagcagacc<br>gctagttattgctcagcggtggc | 33<br>34 |

EXAMPLE 2

The 10 mutants obtained in the example 1 were subjected to SDS-PAGE electrophoresis for expression verification
1. Induced Expression
    (1) Seed culture: 100 μL of bacterial liquid was taken from a glycerin tube and inoculated in a conical flask (10 mL/50 mL) containing a LB liquid medium of Kana (50 μg/mL) according to an inoculation amount of 1%, and cultured for 12 h through oscillation in a constant-temperature shaking table at a speed of 200 rpm and a temperature of 37° C.
    (2) Fermentation culture: the seed liquid was inoculated in a conical flask (100 mL/500 mL) containing a Kana resistant LB liquid medium according to an inoculation amount of 2%, and cultured for 2-3 h in a constant-temperature shaking table at a speed of 180 rpm and a temperature of 37° C. until the optical density $OD_{600}$ reached 0.5-0.6; then 0.25 mM IPTG was added, and induced expression was performed for 12 h at a speed of 180 rpm and a temperature of 30° C.
2. Sample Pretreatment
    (1) 1 mL of bacterial liquid was taken into a 1.5 mL EP tube, and centrifuged for 3 min at a speed of 6,000 rpm and a temperature of 25° C.; the supernatant was discarded.
    (2) 1 mL of a PBS buffer solution with pH of 7.4 was added to resuspend the bacteria.
    (3) The optical density $OD_{600}$ was adjusted to 1.0, 10 μL of 4×Protein Loading Buffer was added into 30 μL of the bacterial solution in (2), and the mixture was oscillated and mixed evenly.
    (4) The mixture was boiled for 10 min.
    (5) The mixture was centrifuged instantaneously for 3 min, 20 μL of the supernatant was taken and loaded as a sample, and subjected to SDS-PAGE gel electrophoresis: 30 min at 90 V, and then 1.5 h at a voltage adjusted to 120 V.
3. Test on the Activity of Nampt Enzyme after Mutation
    (1) Preparation of crude enzyme liquid: 1) 10 mL of bacterial liquid was taken into a 50 mL centrifugal tube, and centrifuged for 20 min at a speed of 4,000 rpm and a temperature of 4° C.; the supernatant was discarded.
    2) 10 mL of a PBS buffer solution with pH of 7.4 was added to blow, beat and resuspend the bacteria, and the bacteria were put in an ice box;
    3) 200 μL of the cell solution in 2) was sucked to a 96-pore ELISA plate, and the optical density $OD_{600}$ of cells was adjusted to 1.0.
    4) 10 mL of the product of 3) was taken and centrifuged for 20 min at a speed of 4,000 rpm and a temperature of 4° C., and re-suspended with 2 mL of a PBS buffer solution and concentrated 5 times.
    5) A clean 25 mL small beaker was prepared, and the cell liquid was poured into the beaker and put in an ice-water bath.
    6) The parameters of an ultrasonic cell disrupter were set as: power of 30%, work for 5s and pause for 5s, and ultrasonic disruption of cells was performed for 10 min.
    7) after the disruption was completed, the supernatant was centrifuged for 20 min at a speed of 4,000 rpm and a temperature of 4° C., to obtain crude enzyme liquid which can be stored in a-20° C. refrigerator.
    (2) Transformation reaction: a transformation system: 12.5 μl of the crude enzyme liquid and 12.5 μl of mother liquid (1 mM NAM, 1 mM PRPP, 1 mM $MnCl_2$, 1 mM $MgCl_2$) were mixed evenly, and allowed to react for 15 min in a shaking table at a speed of 180 rpm and a temperature of 37° C.; then the mixture was heated for 1 min in a metal bath at 95° C., to deactivate the enzyme and terminate the reaction. The product was diluted to 500 μL using a PBS buffer solution with pH of 6.0, centrifuged for 5 min at a speed of 10,000 rpm, filtered with a 0.22 μm microporous filter membrane to remove the bacteria, and then transferred into a liquid-phase vial; and the yield of NMN was measured by HPLC.
    The measurement conditions of HPLC:
    ① D Chromatographic column: ChromCore C18 reversed phase column 5 μm, 4.6×250 mm. Mobile phase: A=phosphate buffer solution (pH 3.5), B=100% methanol.
    Column temperature: 25° C.
    Flow rate: 1.0 mL/min, ultraviolet detection at a wavelength of 260 nm, and a sample size of 20 μL.
    ② Determination of a standard curve
    10-15 mg of a nicotinamide mononucleotide standard was weighed and added with sterile $ddH_2O$ to 25 mL, and diluted with $ddH_2O$ by 10 times, as 100% NMN standard liquid; then the 100% NMN standard liquid was diluted to NMN standard liquids with concentrations of 1%, 10%, 20%, 40%, 60% and 80% respectively; the NMN standard liquids were filtered with a 0.22 μm microporous filter membrane to remove bacteria; the peaking areas of NMN with different concentrations were determined by HPLC; and an NMN standard curve was drawn by taking the NMN concentrations as horizontal coordinates and the peak areas as vertical coordinates.
    ③ NMN in the reaction liquid measured by HPLC
    (1) Pretreatment of sample loading: the transformed liquid after reaction was diluted by 20 times to 500 μl in a 1.5 mL EP tube, and centrifuged for 3 min at a speed of 10,000 rpm and at room temperature; the centrifuged supernatant was sucked with a sterile 1 mL syringe needle, filtered with a disposable sterile 0.22 μm microporous filter membrane to remove bacteria, and transferred into a HPLC-specific liquid-phase vial, to obtain a to-be-measured sample.

(2) The liquid-phase vial was put in an automatic sample loader of HPLC, and the yield of NMN after the enzyme transformation reaction was measured according to the parameters and conditions of HPLC set in ① of the method.

Figure 3:
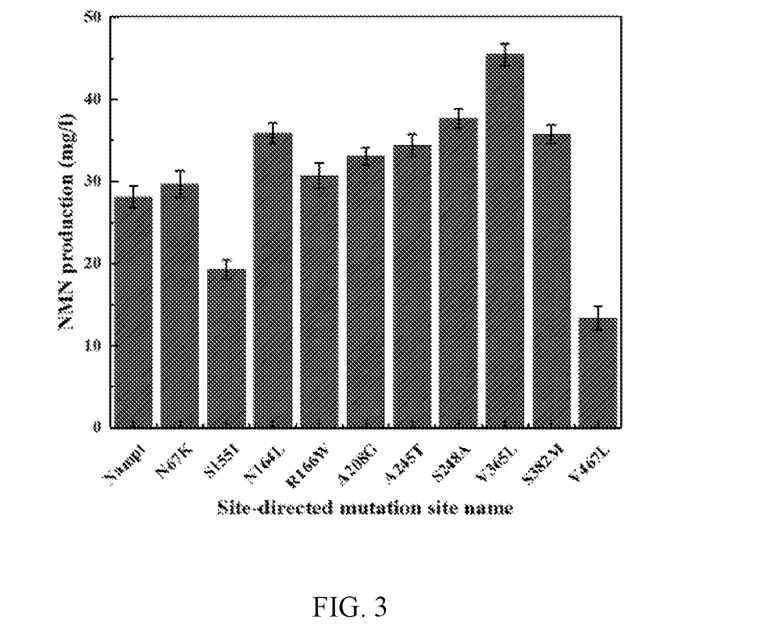
FIG. 3 shows the influence of a strain of Nampt site-directed mutation on the generation of NMN by a transformation reaction.

The results are shown in FIG. 3. Among the designed 10 mutants, the mutants having higher catalytic activity than a wild-type Nampt strain are N67K, N164L, R166W, A208G, A245T, S248A, V365L and S382M. The strains having a decreased catalytic activity are S155I and V476L. Among the mutants, Nampt-V356L has the highest activity. When the mutant Nampt-V356L is used for catalysis, the NMN concentration of the product is 45.42 mg/L, an increase of 62% from that of the wild-type Nampt (around 28.11 mg/L), and the site mutates from neutral nonpolar valine into neutral nonpolar leucine. Therefore, at the position 356 of the gene sequence, leucine has a positive role on enzyme activity. Furthermore, the catalytic activity of the mutant Nampt-S248A is 34% higher than that of the wild-type Nampt strain, indicating that for improving the environment of the region to enhance the stability of Nampt, a hydrophobic amino acid (serine: neutral polar hydrophilic amino acid; alanine: neutral nonpolar hydrophobic amino acid) is beneficial. In addition, the mutants N164L, S382M, A245T and A208G all have a slight increase in activity, and the NMN yields are increased to 35.82 mg/L, 35.75 mg/L, 34.35 mg/L and 33.03 mg/L respectively. The enzyme activity is 27%, 27%, 22% and 17% higher than that of the original strain respectively. The research results also indicate that other mutants have side effects in reducing activity to different extents. For example, as Nampt-V467L mutates from valine to acidic leucine, the enzyme activity is greatly reduced, and the NMN yield of the strain is only 9.31 mg/L; and the NMN yields of Nampt-V467L and Nampt-S155I are reduced by 53% and 31% respectively.

Only preferred embodiments of the present disclosure are described above. It should be noted that those of ordinary skill in the art also may make multiple improvements and modifications without departing from the principles of the present disclosure, and these improvements and modifications should be considered to be within the protection scope of the present disclosure.

What is claimed is:

1. A construction method of a recombinant bacteria expressing a mutant protein of a nicotinamide phosphoribosyltransferase Nampt, wherein the mutant protein of the nicotinamide phosphoribosyltransferase Nampt has only one point mutation on an amino acid sequence of the nicotinamide phosphoribosyltransferase Nampt, the amino acid sequence of the nicotinamide phosphoribosyltransferase Nampt is the sequence as set forth in SEQ ID NO:1, wherein the only one point mutation is any one of N67K, N164L, R166W, A208G, A245T, S248A, V365L and S382M, the construction method comprising the following steps:
  (1) performing a codon optimization on a gene encoding the amino acid sequence of SEQ ID NO:1, to obtain an optimized gene;
  (2) performing a PCR amplification using a site-directed mutation primer and a KOD-Plus-Neo enzyme respectively by taking the optimized gene as a template, to obtain amplification products;
  (3) digesting the amplification products with a DpnI enzyme respectively, and then connecting to the pPSUMO vector respectively, to obtain a recombinant expression vector; and
  (4) transforming the recombinant expression vector into E. coli competent cells respectively, and picking positive clones, to obtain the recombinant bacteria, wherein the site-directed mutation primer in step (2) comprises:

a forward site-directed mutation primer N67K-F and a reverse site-directed mutation primer N67K-R directed at a point mutation of N67K, the nucleotide sequence of the forward site-directed primer N67K-F as set forth in SEQ ID NO: 3, and the nucleotide sequence of the reverse site-directed primer N67K-R as set forth in SEQ ID NO:4;

a forward site-directed mutation primer N164L-F and a reverse site-directed mutation primer N164L-R directed at a point mutation of N164L, the nucleotide sequence of the forward site-directed mutation primer N164L-F as set forth in SEQ ID NO:5, and the nucleotide sequence of the reverse site-directed primer N164L-R as set forth in SEQ ID NO:6;

a forward site-directed mutation primer R166W-F and a reverse site-directed mutation primer R166W-R directed at a point mutation of R166W, the nucleotide sequence of the forward site-directed mutation primer R166W-F as set forth in SEQ ID NO:7, and the nucleotide sequence of the reverse site-directed primer R166W-R as set forth in SEQ ID NO:8;

a forward site-directed mutation primer A208G-F and a reverse site-directed mutation primer A208G-R directed at a point mutation of A208G, the nucleotide sequence of the forward site-directed mutation primer A208G-F as set forth in SEQ ID NO:9, and the nucleotide sequence of the reverse site-directed primer A208G-R as set forth in SEQ ID NO:10;

a forward site-directed mutation primer A245T-F and a reverse site-directed mutation primer A245T-R directed at a point mutation of A245T, the nucleotide sequence of the forward site-directed mutation primer A245T-F as set forth in SEQ ID NO:11, and the nucleotide sequence of the reverse site-directed primer A245T-R as set forth in SEQ ID NO:12;

a forward site-directed mutation primer S248A-F and a reverse site-directed mutation primer S248A-R directed at a point mutation of S248A, the nucleotide sequence of the forward site-directed mutation primer S248A-F as set forth in SEQ ID NO:13, and the nucleotide sequence of the reverse site-directed primer S248A-R as set forth in SEQ ID NO:14;

a forward site-directed mutation primer V365L-F and V365L-R directed at a point mutation of V365L, the nucleotide sequence of the forward site-directed mutation primer V365L-F as set forth in SEQ ID NO:15, and the nucleotide sequence of the reverse site-directed primer V365L-R as set forth in SEQ ID NO:16; or a forward site-directed mutation primer S382M-F and a reverse site-directed mutation primer S382M-R directed at a point mutation of S382M, the nucleotide sequence of the forward site-directed mutation primer S382M-F as set forth in SEQ ID NO:17, and the nucleotide sequence of the reverse site-directed primer S382M-R as set forth in SEQ ID NO:18.

2. The construction method according to claim 1, wherein a nucleotide sequence of the optimized gene in step (1) is the sequence as set forth in SEQ ID NO:2.

3. The construction method according to claim 1, wherein a procedure of the PCR amplification in step (2) comprises: initial denaturation at 94° C. for 2 min, denaturation at 98° C. for 10s, annealing at 55-65° C. for 30s, and extension at 68° C. for 4 min, 30 cycles; and extension at 68° C. for 4 min.

4. The construction method according to claim 1, wherein picking positive clones in step (4) comprises: performing a bacterial liquid PCR using a forward primer Nampt-F and a reverse primer Nampt-R, the nucleotide sequence of the forward primer Nampt-F as set forth in SEQ ID NO: 23, and the nucleotide sequence of the reverse primer Nampt-R as set forth in SEQ ID NO: 24.

5. The construction method according to claim 1, wherein in step (3), the amplification product obtained in step (2) is connected between HindIII and NdeI enzyme digestion sites of the pPSUMO vector.

6. The construction method according to claim 1, wherein in step (3), the obtained recombinant expression vector comprises a nucleotide sequence encoding the mutant protein, and wherein the nucleotide sequence of the recombinant expression vector has the sequence as set forth in SEQ ID NO:2 with base changes compared of 202_204aac>aaa corresponding to N67K, 493_495aac>ctg corresponding to N164L, 499_501cgc>tgg corresponding to R166W, 625_627gct>ggc corresponding to A208G, 736_738gct>acc corresponding to A245T, 745_747tca>gcg corresponding to S248A, 1096_1098gtt>ctg corresponding to V365L, or 1147_1149tca>atg corresponding to S382M.

* * * * *

SEQUENCE LISTING

```
Sequence total quantity: 34
SEQ ID NO: 1            moltype = AA   length = 491
FEATURE                 Location/Qualifiers
REGION                  1..491
                        note = synthetic
source                  1..491
                        mol_type = protein
                        organism = synthetic construct
SEQUENCE: 1
GNAAAEAEFN ILLATDSYKV THYKQYPPNT SKVYSYFECR EKKTENSKVR KVKYEETVFY   60
GLQYILNKYL KGKVVTKEKI QEAKEVYREH FQDDVFNERG WNYILEKYDG HLPIEVKAVP  120
EGSVIPRGNV LFTVENTDPE CYWLTNWIET ILVQSWYPIT VATNSREQKK ILAKYLLETS  180
GNLDGLEYKL HDFGYRGVSS QETAGIGASA HLVNFKGTDT VAGIALIKKY YGTKDPVPGY  240
SVPAAEHSTI TAWGKDHEKD AFEHIVTQFS SVPVSVVSDS YDIYNACEKI WGEDLRHLIV  300
SRSTEAPLII RPDSGNPLDT VLKVLDILGK KFPVTENSKG YKLLPPYLRV IQGDGVDINT  360
LQEIVEGMKQ KKWSIENVSF GSGGALLQKL TRDLLNCSFK CSYVVTNGLG VNVFKDPVAD  420
PNKRSKKGRL SLHRTPAGNF VTLEEGKGDL EEYGHDLLHT VFKNGKVTKS YSFDEVRKNA  480
QLNIEQDVAP H                                                      491

SEQ ID NO: 2            moltype = DNA   length = 1482
FEATURE                 Location/Qualifiers
misc_feature            1..1482
                        note = synthetic
source                  1..1482
                        mol_type = other DNA
                        organism = synthetic construct
SEQUENCE: 2
catatgaacg ctgctgctga ggccgagttc aatatattgt tagcgaccga ctcgtacaag   60
gtcacgcatt ataaacagta tcctcctaac acatcaaagg tctactcata tttcgagtgc  120
cgcgagaaga agacggagaa ctcgaaagtc cgaaaggtga agtatgaaga aacagtgttc  180
tacgggcttc agtatattct taacaaatat cttaaaggca aagttgttac aaaggagaag  240
atccaggaag ctaaagaagt ttatcgcgaa catttccaag acgatgtctt caatgagcgc  300
ggctggaact atattcttga gaagtacgac ggccatcttc ctattgaagt taaagctgtt  360
cctgaaggct cagttattcc tcgcggcaac gtcctgttta ccgtcgagaa tacggatcct  420
gaatgttatt ggcttacaaa ctggattgaa acaattcttg ttcagtcatg gtatcctatt  480
acagttgcta caaactcacg cgaacagaag aagatcctag ctaaatatct tcttgaaaca  540
tcaggcaacc ttgatggcct tgaatataaa cttcatgatt tcgggtaccg cggcgtttca  600
tcacaggaaa cagctggcat tggcgcttca gctcatcttg ttaactttaa aggcacagat  660
acagttgctg gcattgctct tattaagaag tactacggca caaaggaccc agttcctggt  720
tattcagttc ctgctgctga acattcaaca attacagctt ggggaaagga tcatgagaag  780
gacgcgttcg agcacattgt tacacagttc agtagtgttc ctgtttcagt tgtttcagat  840
tcttatgata tttataacgc ttgtgagaag atctggggag aggaccttcg ccatcttatt  900
gtttcacgct caacagaagc tcctcttatt attcgccctg attcaggcaa ccctcttgat  960
acagttctta aagttcttga tattcttggc aagaagttcc cggttaccga gaattccaag 1020
ggttataaac ttcctcctcc ttatcttcgc gttattcagg gcgatggcgt tgatattaac 1080
acacttcagg aaattgttga aggcatgaaa cagaagaagt ggtccattga gaatgtctca 1140
tttggctcag gcggcgctct tcttcagaaa cttacgcgg atcttcttaa ctgttcatttt 1200
aaatgttctt atgttgttac aaacggcctt ggcgttaacg tgttcaaaga tcccgtagca 1260
gaccctaaca aacgctcaaa gaagggtcga ctttcacttc atcgcacacc tgctggcaac 1320
tttgttacac ttgaagaagg caaaggcgat cttgaagaat atggccatga tcttcttcat 1380
```

```
acagtgttca agaatggcaa ggtaacgaag tcctactcat ttgatgaagt tcgcaagaat    1440
gcgcagctta acattgaaca ggatgttgct cctcataagc tt                       1482

SEQ ID NO: 3           moltype = DNA   length = 36
FEATURE                Location/Qualifiers
misc_feature           1..36
                       note = synthetic
source                 1..36
                       mol_type = other DNA
                       organism = synthetic construct
SEQUENCE: 3
cgggcttcag tatattctta aaaaatatct taaagg                              36

SEQ ID NO: 4           moltype = DNA   length = 33
FEATURE                Location/Qualifiers
misc_feature           1..33
                       note = synthetic
source                 1..33
                       mol_type = other DNA
                       organism = synthetic construct
SEQUENCE: 4
tttaagaata tactgaagcc cgtagaacac tgt                                 33

SEQ ID NO: 5           moltype = DNA   length = 31
FEATURE                Location/Qualifiers
misc_feature           1..31
                       note = synthetic
source                 1..31
                       mol_type = other DNA
                       organism = synthetic construct
SEQUENCE: 5
cctattacag ttgctacact gtcacgcgaa c                                   31

SEQ ID NO: 6           moltype = DNA   length = 28
FEATURE                Location/Qualifiers
misc_feature           1..28
                       note = synthetic
source                 1..28
                       mol_type = other DNA
                       organism = synthetic construct
SEQUENCE: 6
cagtgtagca actgtaatag gataccat                                       28

SEQ ID NO: 7           moltype = DNA   length = 30
FEATURE                Location/Qualifiers
misc_feature           1..30
                       note = synthetic
source                 1..30
                       mol_type = other DNA
                       organism = synthetic construct
SEQUENCE: 7
gttgctacaa actcatggga acagaagaag                                     30

SEQ ID NO: 8           moltype = DNA   length = 32
FEATURE                Location/Qualifiers
misc_feature           1..32
                       note = synthetic
source                 1..32
                       mol_type = other DNA
                       organism = synthetic construct
SEQUENCE: 8
ccatgagttt gtagcaactg taataggata cc                                  32

SEQ ID NO: 9           moltype = DNA   length = 33
FEATURE                Location/Qualifiers
misc_feature           1..33
                       note = synthetic
source                 1..33
                       mol_type = other DNA
                       organism = synthetic construct
SEQUENCE: 9
ggaaacagct ggcattggcg gctcagctca tct                                 33

SEQ ID NO: 10          moltype = DNA   length = 33
FEATURE                Location/Qualifiers
misc_feature           1..33
                       note = synthetic
source                 1..33
                       mol_type = other DNA
```

```
                          organism = synthetic construct
SEQUENCE: 10
gccgccaatg ccagctgttt cctgtgatga aac                                  33

SEQ ID NO: 11           moltype = DNA   length = 35
FEATURE                 Location/Qualifiers
misc_feature            1..35
                        note = synthetic
source                  1..35
                        mol_type = other DNA
                        organism = synthetic construct
SEQUENCE: 11
cctggttatt cagttcctgc taccgaacat tcaac                                35

SEQ ID NO: 12           moltype = DNA   length = 29
FEATURE                 Location/Qualifiers
misc_feature            1..29
                        note = synthetic
source                  1..29
                        mol_type = other DNA
                        organism = synthetic construct
SEQUENCE: 12
ggtagcagga actgaataac caggaactg                                       29

SEQ ID NO: 13           moltype = DNA   length = 29
FEATURE                 Location/Qualifiers
misc_feature            1..29
                        note = synthetic
source                  1..29
                        mol_type = other DNA
                        organism = synthetic construct
SEQUENCE: 13
tcctgctgct gaacatgcga caattacag                                       29

SEQ ID NO: 14           moltype = DNA   length = 29
FEATURE                 Location/Qualifiers
misc_feature            1..29
                        note = synthetic
source                  1..29
                        mol_type = other DNA
                        organism = synthetic construct
SEQUENCE: 14
actatgttca gcagcaggaa ctgaataac                                       29

SEQ ID NO: 15           moltype = DNA   length = 37
FEATURE                 Location/Qualifiers
misc_feature            1..37
                        note = synthetic
source                  1..37
                        mol_type = other DNA
                        organism = synthetic construct
SEQUENCE: 15
attaacacac ttcaggaaat tctggaaggc atgaaac                              37

SEQ ID NO: 16           moltype = DNA   length = 31
FEATURE                 Location/Qualifiers
misc_feature            1..31
                        note = synthetic
source                  1..31
                        mol_type = other DNA
                        organism = synthetic construct
SEQUENCE: 16
cagaatttcc tgaagtgtgt taatatcaac g                                    31

SEQ ID NO: 17           moltype = DNA   length = 34
FEATURE                 Location/Qualifiers
misc_feature            1..34
                        note = synthetic
source                  1..34
                        mol_type = other DNA
                        organism = synthetic construct
SEQUENCE: 17
attgagaatg tctcatttgg catgggcggc gctc                                 34

SEQ ID NO: 18           moltype = DNA   length = 29
FEATURE                 Location/Qualifiers
misc_feature            1..29
                        note = synthetic
source                  1..29
```

```
                            mol_type = other DNA
                            organism = synthetic construct
SEQUENCE: 18
catgccaaat gagacattct caatggacc                                              29

SEQ ID NO: 19           moltype = DNA   length = 36
FEATURE                 Location/Qualifiers
misc_feature            1..36
                        note = synthetic
source                  1..36
                        mol_type = other DNA
                        organism = synthetic construct
SEQUENCE: 19
ggattgaaac aattcttgtt cagatctggt atccta                                      36

SEQ ID NO: 20           moltype = DNA   length = 32
FEATURE                 Location/Qualifiers
misc_feature            1..32
                        note = synthetic
source                  1..32
                        mol_type = other DNA
                        organism = synthetic construct
SEQUENCE: 20
gatctgaaca agaattgttt caatccagtt tg                                          32

SEQ ID NO: 21           moltype = DNA   length = 36
FEATURE                 Location/Qualifiers
misc_feature            1..36
                        note = synthetic
source                  1..36
                        mol_type = other DNA
                        organism = synthetic construct
SEQUENCE: 21
agtgttcaag aatggcaagc tgacgaagtc ctactc                                      36

SEQ ID NO: 22           moltype = DNA   length = 33
FEATURE                 Location/Qualifiers
misc_feature            1..33
                        note = synthetic
source                  1..33
                        mol_type = other DNA
                        organism = synthetic construct
SEQUENCE: 22
cagcttgcca ttcttgaaca ctgtatgaag aag                                         33

SEQ ID NO: 23           moltype = DNA   length = 34
FEATURE                 Location/Qualifiers
misc_feature            1..34
                        note = synthetic
source                  1..34
                        mol_type = other DNA
                        organism = synthetic construct
SEQUENCE: 23
taatccttat tcagtggtgg tggtggtggt gctc                                        34

SEQ ID NO: 24           moltype = DNA   length = 29
FEATURE                 Location/Qualifiers
misc_feature            1..29
                        note = synthetic
source                  1..29
                        mol_type = other DNA
                        organism = synthetic construct
SEQUENCE: 24
aggaagcttg catatgaacg ctgctgctg                                              29

SEQ ID NO: 25           moltype = DNA   length = 27
FEATURE                 Location/Qualifiers
misc_feature            1..27
                        note = synthetic
source                  1..27
                        mol_type = other DNA
                        organism = synthetic construct
SEQUENCE: 25
aaaggtctac tcatatttcg agtgccg                                                27

SEQ ID NO: 26           moltype = DNA   length = 23
FEATURE                 Location/Qualifiers
misc_feature            1..23
                        note = synthetic
```

```
source                  1..23
                        mol_type = other DNA
                        organism = synthetic construct
SEQUENCE: 26
tctgttcgcg tgagtttgta gca                                              23

SEQ ID NO: 27           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 27
gtacgacggc catcttccta ttga                                             24

SEQ ID NO: 28           moltype = DNA  length = 23
FEATURE                 Location/Qualifiers
misc_feature            1..23
                        note = synthetic
source                  1..23
                        mol_type = other DNA
                        organism = synthetic construct
SEQUENCE: 28
gaactgggtc ctttgtgccg tag                                              23

SEQ ID NO: 29           moltype = DNA  length = 23
FEATURE                 Location/Qualifiers
misc_feature            1..23
                        note = synthetic
source                  1..23
                        mol_type = other DNA
                        organism = synthetic construct
SEQUENCE: 29
ggcgcttcag ctcatcttgt taa                                              23

SEQ ID NO: 30           moltype = DNA  length = 26
FEATURE                 Location/Qualifiers
misc_feature            1..26
                        note = synthetic
source                  1..26
                        mol_type = other DNA
                        organism = synthetic construct
SEQUENCE: 30
tgaataacgc gaagataagg aggaag                                           26

SEQ ID NO: 31           moltype = DNA  length = 23
FEATURE                 Location/Qualifiers
misc_feature            1..23
                        note = synthetic
source                  1..23
                        mol_type = other DNA
                        organism = synthetic construct
SEQUENCE: 31
agaggacctt cgccatctta ttg                                              23

SEQ ID NO: 32           moltype = DNA  length = 23
FEATURE                 Location/Qualifiers
misc_feature            1..23
                        note = synthetic
source                  1..23
                        mol_type = other DNA
                        organism = synthetic construct
SEQUENCE: 32
aggacttcgt taccttgcca ttc                                              23

SEQ ID NO: 33           moltype = DNA  length = 23
FEATURE                 Location/Qualifiers
misc_feature            1..23
                        note = synthetic
source                  1..23
                        mol_type = other DNA
                        organism = synthetic construct
```

-continued

```
SEQUENCE: 33
gttcaaagat cccgtagcag acc                                            23

SEQ ID NO: 34          moltype = DNA  length = 23
FEATURE                Location/Qualifiers
misc_feature           1..23
                       note = synthetic
source                 1..23
                       mol_type = other DNA
                       organism = synthetic construct
SEQUENCE: 34
gctagttatt gctcagcggt ggc                                            23
```